US009552681B2

United States Patent
Burger

(10) Patent No.: US 9,552,681 B2
(45) Date of Patent: Jan. 24, 2017

(54) APPARATUS FOR ASSESSING OR MITIGATING INSURANCE RISK

(71) Applicant: Alcohol Countermeasure Systems (International) Inc., Toronto (CA)

(72) Inventor: William Joseph Burger, Mississauga (CA)

(73) Assignee: Alcohol Countermeasure Systems (International) Inc., Toronto (CA)

( * ) Notice: Subject to any disclaimer, the term of this patent is extended or adjusted under 35 U.S.C. 154(b) by 0 days.

(21) Appl. No.: 14/454,770

(22) Filed: Aug. 8, 2014

(65) Prior Publication Data

US 2015/0081134 A1     Mar. 19, 2015

Related U.S. Application Data

(60) Provisional application No. 61/863,636, filed on Aug. 8, 2013.

(51) Int. Cl.
*G07C 5/02* (2006.01)
*A61B 5/08* (2006.01)
*A61B 10/00* (2006.01)
*G07C 5/08* (2006.01)

(52) U.S. Cl.
CPC ............... *G07C 5/02* (2013.01); *A61B 10/00* (2013.01); *A61B 5/082* (2013.01); *A61B 2010/0003* (2013.01); *A61B 2010/0009* (2013.01); *A61B 2010/0087* (2013.01); *G07C 5/0858* (2013.01)

(58) Field of Classification Search
CPC ................................ G07C 5/02; B60K 28/063
USPC ............................................................. 701/1
See application file for complete search history.

(56) References Cited

U.S. PATENT DOCUMENTS

| 4,868,545 A | * | 9/1989 | Jones | G01N 33/4972 340/573.1 |
| 6,064,970 A | * | 5/2000 | McMillan | G06Q 30/0283 340/439 |
| 6,697,732 B1 | * | 2/2004 | Gotfried | B60K 28/063 180/272 |
| 6,730,494 B1 | * | 5/2004 | Toranto | G01N 33/98 206/204 |
| 6,853,956 B2 | * | 2/2005 | Ballard, Jr. | B60K 28/063 180/272 |

(Continued)

OTHER PUBLICATIONS

Webpages, The Globe and Mail, Young Drivers, Insurance industry's driver monitoring device is habit-forming, obtained from: URL:<http://www.theglobeandmail.com/globe-drive/news/industry-news/insurance-industrys-driver-monitoring-device-is-habit-forming/article18804860/>, 2 pages, dated May 26, 2014.

*Primary Examiner* — Behrang Badii
*Assistant Examiner* — Michael Berns
(74) *Attorney, Agent, or Firm* — Lipsitz & McAllister, LLC

(57) ABSTRACT

The apparatus, which is used with a vehicle, comprises a breath alcohol sensor and a computing device. The computing device is operatively coupled in use to the sensor and the vehicle and configured to record data: which provides information indicative of the likelihood that the vehicle has been operated in circumstances wherein a breath sample has not been delivered to the sensor within a predetermined period preceding the commencement of said operation; and associated with the delivery of breath samples to the sensor that contain alcohol in excess of a predetermined threshold.

7 Claims, 4 Drawing Sheets

(56) References Cited

U.S. PATENT DOCUMENTS

| | | | | |
|---|---|---|---|---|
| 7,287,617 | B2* | 10/2007 | Mobley | G01N 33/4972 180/272 |
| 8,311,858 | B2* | 11/2012 | Everett | G06Q 40/08 246/45 |
| 8,381,573 | B2* | 2/2013 | Keays | 422/84 |
| 2006/0212195 | A1 | 9/2006 | Veith et al. | |
| 2013/0206495 | A1* | 8/2013 | Westbrook | B60K 28/063 180/272 |

* cited by examiner

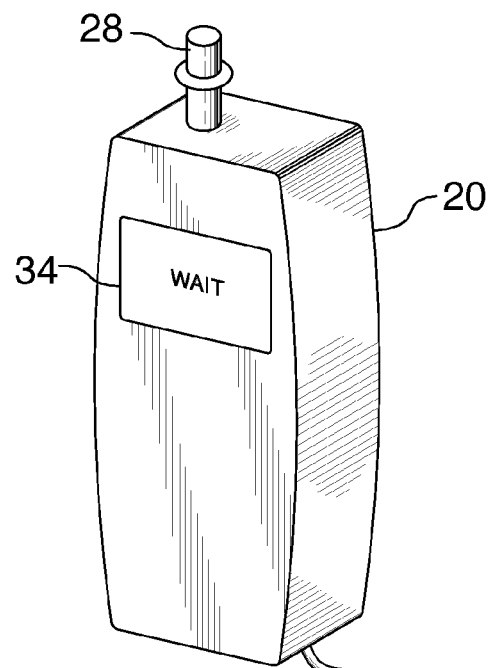
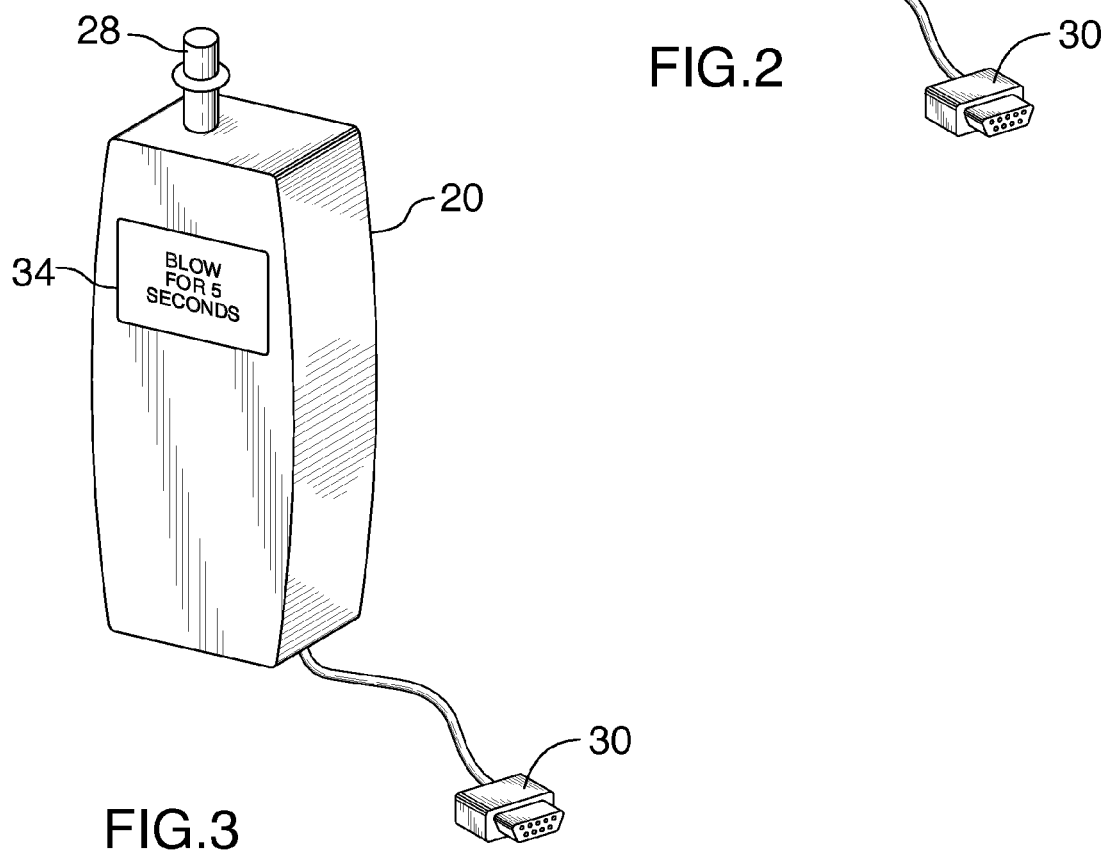
FIG.2
FIG.3

APPARATUS FOR ASSESSING OR MITIGATING INSURANCE RISK

The present application claims the benefit of U.S. provisional patent application No. 61/863,636 filed on Aug. 8, 2013, which is incorporated herein and made a part hereof by reference in its entirety and for all purposes.

FIELD OF THE INVENTION

The invention relates to the field of vehicle insurance.

BACKGROUND OF THE INVENTION

It is well-known to secure a motor vehicle against operation by a person who has consumed alcohol by installing in said vehicle a breath alcohol tester. A typical arrangement, known as an ignition interlock device (IID), involves a relay between the breath tester and the starter motor, pursuant to which the starter motor cannot be engaged until a satisfactory breath sample has been given. In this regard, a 'satisfactory' gas sample is conventionally understood to be one that (I) is of sufficient volume and pressure to permit alcohol analysis; (II) has alcohol concentration below a predetermined limit; and (III) appears to have originated from the exhaled breath of a human being. Criterion (III) is often assessed through measurements of pressure, humidity and temperature, but various other techniques such as hum recognition sensors are occasionally used. In some jurisdictions, a person convicted of driving under the influence of alcohol may be required by law to have a device of this type installed as a condition associated with the extension of driving privileges.

SUMMARY OF THE INVENTION

Forming one aspect of the invention is an apparatus for use with a vehicle. This apparatus comprises a breath alcohol sensor and a computing device operatively coupled in use to the sensor and the vehicle. The computing device is configured to record data: which provides information indicative of the likelihood that the vehicle has been operated in circumstances wherein a breath sample has not been delivered to the sensor within a predetermined period preceding the commencement of said operation; and associated with the delivery of breath samples to the sensor that contain alcohol in excess of a predetermined threshold.

According to another aspect of the invention, the predetermined threshold can be less than the impaired driving threshold.

According to another aspect of the invention, the computing device can be coupled to the vehicle in use via a standardized communication port of the vehicle which provides real time data about the vehicle.

According to another aspect of the invention, the period preceding the commencement of operation can be defined with reference to one or more of:
 i. information regarding vehicle running status obtained from the port;
 ii. information regarding engine RPM obtained from the port; and
 iii. information regarding vehicle distance traveled obtained from the port.

According to another aspect of the invention, the device can record any periods in which the apparatus is coupled to a vehicle.

According to another aspect of the invention, the device can record any periods in which the apparatus is coupled to a vehicle and the vehicle to which it is then coupled.

According to another aspect of the invention, the port can be an OBD-II port.

Further features and advantages associated with the invention will become apparent upon review of the following detailed description and the appended drawings, the latter being briefly described hereinafter.

BRIEF DESCRIPTION OF THE DRAWINGS

FIG. 2 is a view of a display screen on the device showing the message displayed in one condition;

FIG. 3 is a similar to FIG. 2 showing another message;

DETAILED DESCRIPTION OF THE EXEMPLARY EMBODIMENT

Figure 1:
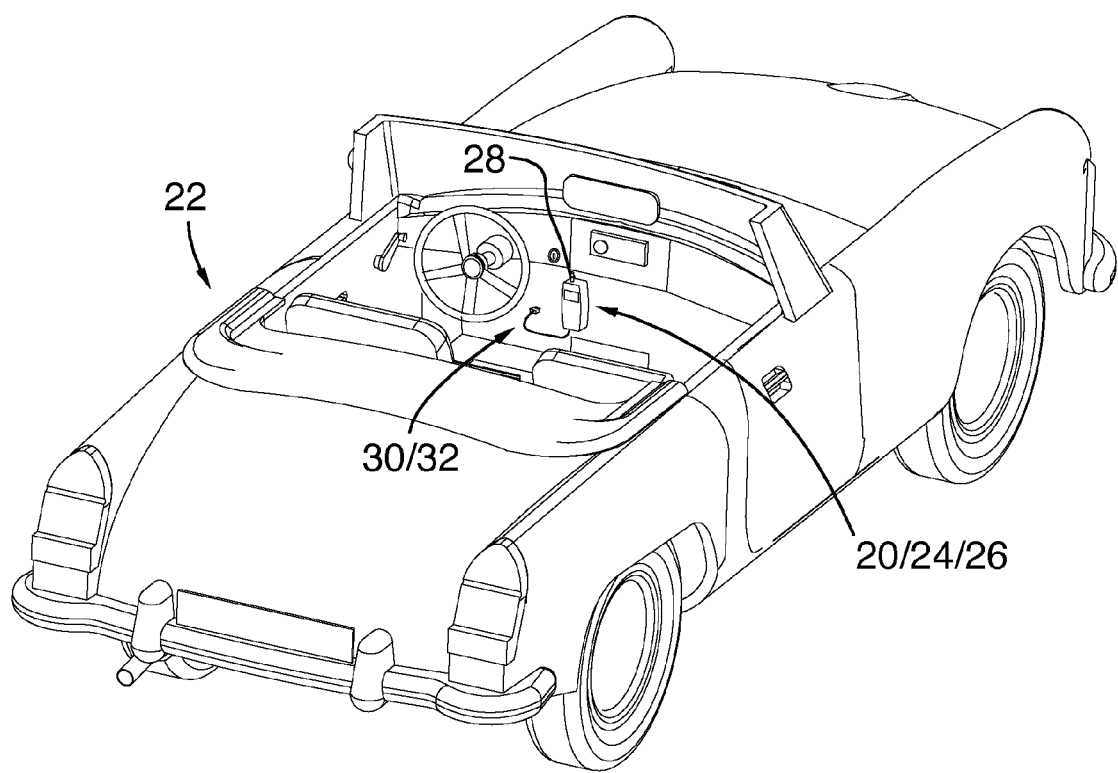
FIG. 1 is a view of apparatus according to an exemplary embodiment of the invention in use with a vehicle.

The exemplary embodiment shown in use in association with a vehicle 22 in FIG. 1 will be seen to include a handset 20 which will be understood to house a breath alcohol sensor 24 and a computing device 26. A breath sampling tube 28 projects from the top of the handset.

Vehicle 22 forms no part of the invention and is illustrated for clarity, only.

The breath alcohol sensor 24 is of the conventional fuel cell type that is commonly used in breath alcohol testers and in this embodiment is electronically coupled to the computing device 26 internally of the handset 20. It is well known to couple breath alcohol sensors to computing devices in, for example, handheld breath alcohol testers and breath alcohol interlock devices and accordingly, further description of such coupling is neither required nor provided.

This computing device 26 is coupled to the vehicle, via an OBD-II plug 30 coupled to the OBD-II port 32 of the vehicle 22, and is configured to record data: (i) which provides information indicative of the likelihood that the vehicle has been operated in circumstances wherein a breath sample has not been delivered to the sensor within a predetermined period preceding the commencement of said operation; and (ii) associated with the delivery of breath samples to the sensor that contain alcohol in excess of a predetermined threshold that is less than the impaired driving threshold applicable in the jurisdiction of use.

More particularly in respect of each instance wherein the operation of the vehicle is commenced, the device records the following details:
 i. satisfactory breath sample delivered to the device in the predetermined period preceding the commencement of said operation
 ii. no breath sample delivered to the device in the predetermined period preceding the commencement of said operation
 iii. unsatisfactory breath sample delivered to the device in the predetermined period preceding the commencement of said operation and associated failure criterion, i.e. (I), (II) and/or (III) from above In the exemplary embodiment, the period preceding the commencement of operation is defined with reference to information regarding vehicle running status obtained from the OBD system and the device records any periods in which the apparatus is coupled to a vehicle and the vehicle to which it is coupled, again, with reference to information obtained from the OBD system.

For greater certainty, it will be appreciated that information that the apparatus has been uncoupled from the vehicle is indicative of the likelihood that the vehicle has been operated in circumstances wherein a breath sample has not been delivered to the sensor within a predetermined period preceding the commencement of said operation.

When it is desired to put a vehicle into operation:

STEP 1 the operator unlocks the vehicle, which commences a warm-up procedure by which the sensor is rendered active; during this period, the apparatus directs the operator to "wait" by way of a text message on a display screen 34 of the apparatus, as per FIG. 2

STEP 2 once the sensor is ready to receive a sample, the apparatus directs the operator to deliver a sample, again, via the display screen 34, as per FIG. 3

STEP 3 on receipt of a breath sample, the apparatus detects if the sample is satisfactory, i.e. meets aforementioned criteria (I), (II) and (III)

Figure 4:
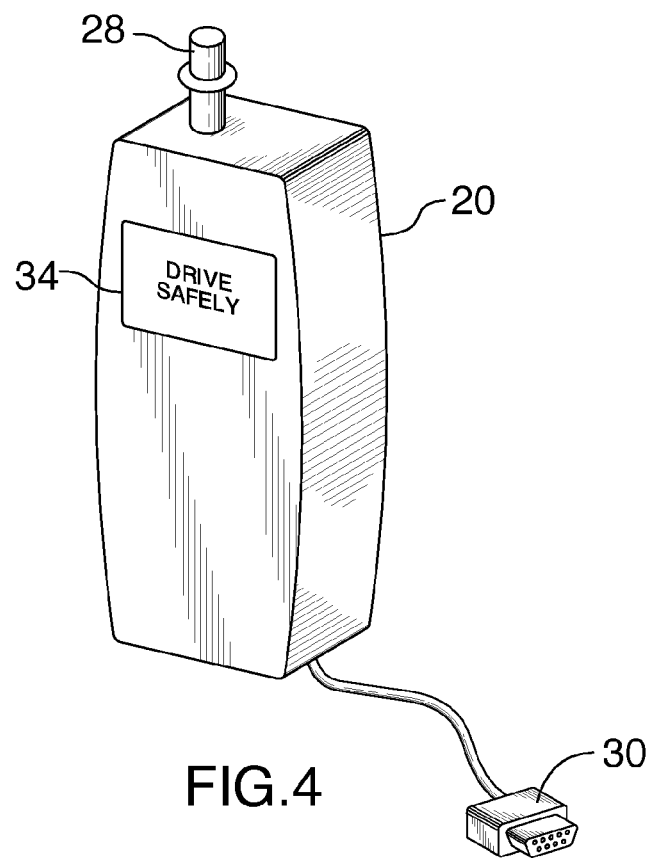
FIG. 4 is a view similar to FIG. 2 showing another message.

STEP 4A if the apparatus detects the sample to be satisfactory, the device signals to the driver that the vehicle can be put into operation, through a message on the display screen, as per FIG. 4

Figure 5:
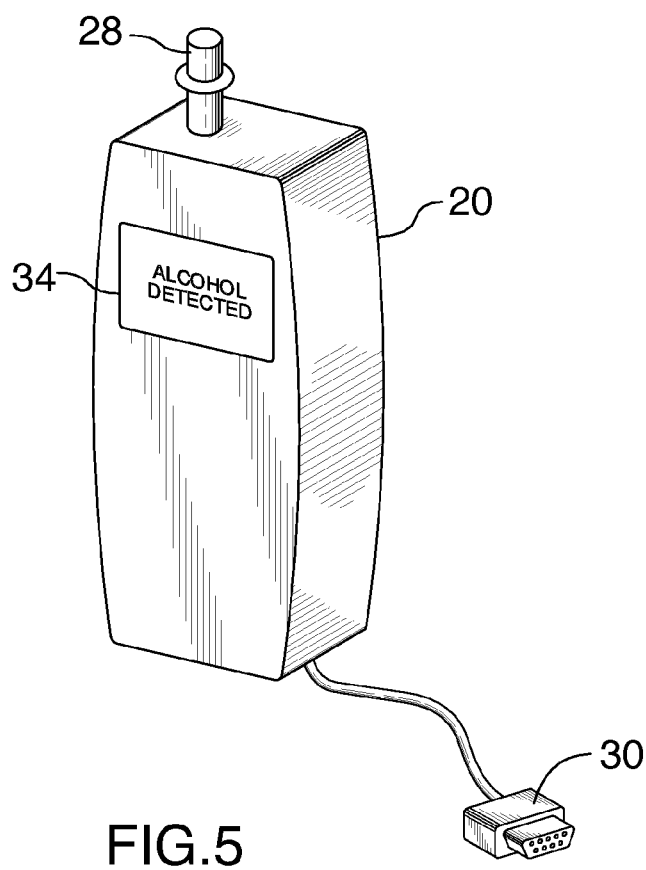
FIG. 5 is a view similar to FIG. 2 showing another message.
Figure 6:
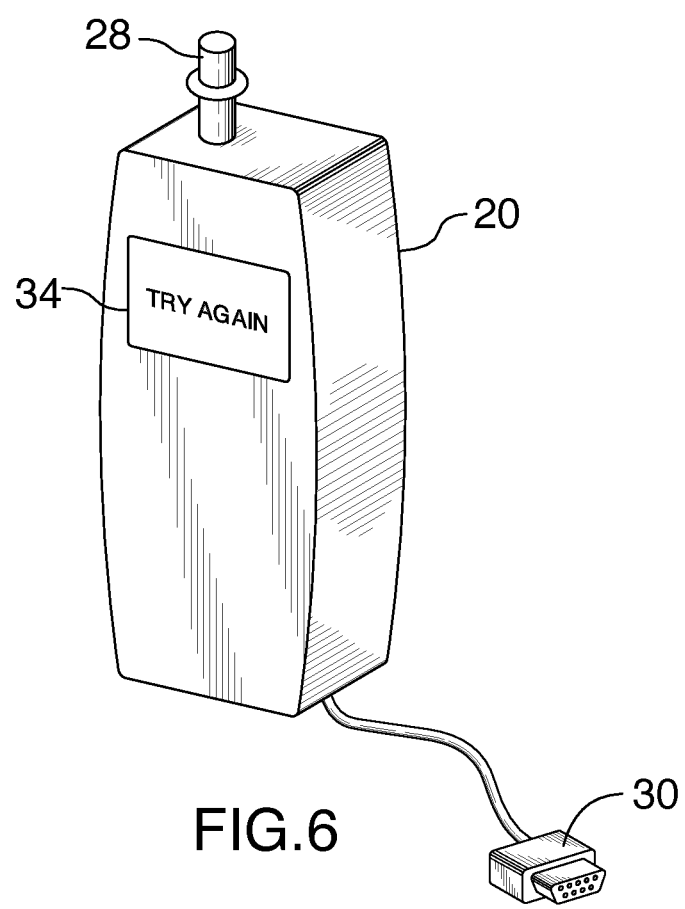
FIG. 6 is a view similar to FIG. 2 showing another message.

STEP 4B if the apparatus detects the sample to be unsatisfactory for reason of alcohol concentration above the threshold, the device indicates as much to the driver, through a message on the display screen, as per FIG. 5 and returns to STEP 2 after a predetermined lockout period of 5 minutes has elapsed STEP 4C if the apparatus detects the sample to be unsatisfactory for reasons other than alcohol concentration, the device indicates as much to the driver, through a message on the display screen, as per FIG. 6, and returns to STEP 2 after a predetermined lockout period of 30 seconds has elapsed When the doors of the vehicle are locked and the vehicle is brought to rest, the display screen 34 is deactivated and the apparatus reverts to a low-power consumption mode.

It is notable that the exemplary apparatus does not record breath alcohol concentration in excess of the predetermined threshold, nor does it restrict operation of the vehicle at any time.

The exemplary apparatus has advantage in that it facilitates the delivery to an insurance company of proof that a driver does not drive a vehicle under the influence of alcohol in a manner that provides security to the driver that any evidence collected will not be used to his or her prejudice, since the apparatus does not collect proof of levels of alcohol consumption associated with criminal operation of a vehicle nor impairment.

In an exemplary method using the apparatus:

a third party makes apparatus of the aforementioned functionality available to an insurer a person desirous of obtaining insurance on a reduced premium basis from the insurer is referred to the third party and attends at the premises of the third party to obtain the apparatus therefrom the apparatus is installed in the vehicle of the person by the third party at the end of a period prescribed by the insurer, the person attends at the premises of the third party and the apparatus is removed from the vehicle the data collected by the device is extracted from the device in a conventional manner and delivered to the insurer in a useful format Data extraction from breath alcohol interlock devices is well known and accordingly, further details as to the data extraction is neither provided nor required.

The form of report delivered to the insurer could take any form as desired by the insurer and could include data such as:

number of vehicle starts in total and per day number of failed alcohol tests in total and per day distance driven in total and per day distance driven with failed alcohol test Whereas but a single embodiment is shown and described, variations are possible.

For example, whereas in the exemplary embodiment, the period preceding commencement of operation is defined with reference to information regarding vehicle running status obtained from the OBD system, the period could be defined by, for example: information regarding engine RPM obtained from the OBD system; information regarding vehicle distance traveled obtained from the OBD system; or information regarding vehicle distance traveled obtained from GPS.

In the case of GPS-based information, the "operative coupling" of the apparatus and the car would be by way of communication signals between the GPS transmitter on the vehicle, the GPS receiver on the satellite and a communication link between the GPS receiver and the computing functionality. The communication link could, for example, be indirect: the third party provider could, for example, receive the GPS location information of the vehicle in real time and the breath test data in batch and synchronize the results to produce the aforementioned reports.

As well, whereas in the exemplary embodiment, the apparatus couples to the OBD-II port, the apparatus could couple with similar functionality to any standardized communication port of the vehicle which provides real time data about the vehicle sufficient to ascertain vehicle operation. Alternatively, the apparatus could be "hard wired" to suitable circuitry in the vehicle to collect information, such as the ignition relay, transmission sensor or odometer.

Further, whereas a 5 minute lockout period is indicated in the exemplary embodiment, this period could be shorter, longer or omitted altogether. A 5 minute lockout is believed to be reasonable, since it allows sufficient time, for example, for errant mouth alcohol to dissipate.

As well, whereas the exemplary embodiment of the apparatus is triggered by the vehicle locking mechanism, the warm-up period could similarly be manually triggered by a "start" button or the like or activity on the part of the apparatus could be tied to activity of the OBD system or of the vehicle itself.

Additionally, a warning state could be triggered if the vehicle is put into motion in the absence of a suitable breath sample, if the operator, for example, forgot to deliver a sample; a suitable sample delivered shortly after commencement of operation might be viewed as curing the fault.

Yet further, whereas the apparatus of the exemplary embodiment does not collect alcohol measurements in excess of the predetermined threshold, this functionality could be incorporated, if desired.

It will also be appreciated that security and encryption methodologies could be employed by the apparatus to hinder tampering. Evidence of tampering would also be information indicative of the likelihood that the vehicle has been operated in circumstances wherein a breath sample has not been delivered to the sensor within a predetermined period preceding the commencement of said operation. Persons of ordinary skill in the art of alcohol interlock design are familiar with anti-tampering technology and accordingly, further detail is neither required nor provided.

As well, whereas a display screen is shown in the illustrations, the various messages and prompts could, for example, be signalled by appropriately labelled lights In view of all the above, the invention will be understood as limited only by the accompanying claims, purposively construed.

The invention claimed is:

1. A method for assessing or mitigating insurance risk, comprising:
   providing a breath alcohol sensor for use in a vehicle owned or operated by an insured;
   providing a computing device operatively coupled in use to the sensor and the vehicle and configured for recording data, the data comprising:
      data which provides information regarding periods when the computing device is coupled to the vehicle and a breath sample has not been delivered to the sensor within a predetermined period preceding a commencement of operation of the vehicle;
      data which provides information regarding periods when the computing device is uncoupled from the vehicle; and
      data associated with breath samples delivered to the sensor that contain alcohol in excess of a predetermined threshold that is less than an impaired driving threshold applicable in a jurisdiction of use; and
   providing the recorded data to an insurer;
   wherein the computing device is adapted to permit operation of the vehicle both when the breath sample is delivered to the sensor and when the breath sample has not been delivered to the sensor; and
   the data does not include data indicating that the breath sample contains alcohol at a level exceeding the impaired driving threshold.

2. The method in accordance with claim 1, further comprising:
   analyzing of the recorded data by the insurer to compute an availability of a reduced insurance premium for the insured.

3. The method in accordance with claim 1, wherein the computing device is coupled to the vehicle in use via a standardized communication port of the vehicle which provides real time data about the vehicle.

4. The method in accordance with claim 3, wherein the predetermined period preceding the commencement of operation is defined with reference to one or more of: information regarding vehicle running status obtained from the port; information regarding engine RPM obtained from the port; and information regarding vehicle distance traveled obtained from the port.

5. The method in accordance with claim 3, wherein the port comprises an OBD-II port.

6. The method in accordance with claim 1, wherein the computing device records the data during any periods in which the apparatus is coupled to the vehicle.

7. The method in accordance with claim 1, wherein the computing device records the data during any periods in which the apparatus is coupled to the vehicle and information regarding any vehicles to which it is coupled.

* * * * *